United States Patent
Gil

(10) Patent No.: US 8,167,960 B2
(45) Date of Patent: May 1, 2012

(54) METHOD OF REMOVING CARBON DIOXIDE EMISSIONS FROM IN-SITU RECOVERY OF BITUMEN AND HEAVY OIL

(75) Inventor: Henry Gil, Calgary (CA)

(73) Assignee: Osum Oil Sands Corp. (CA)

( * ) Notice: Subject to any disclaimer, the term of this patent is extended or adjusted under 35 U.S.C. 154(b) by 691 days.

(21) Appl. No.: 12/255,503

(22) Filed: Oct. 21, 2008

(65) Prior Publication Data

US 2009/0100754 A1    Apr. 23, 2009

Related U.S. Application Data

(60) Provisional application No. 60/981,724, filed on Oct. 22, 2007, provisional application No. 60/990,519, filed on Nov. 27, 2007.

(51) Int. Cl.
| | |
|---|---|
| B01D 53/48 | (2006.01) |
| C01B 3/32 | (2006.01) |
| C01C 1/00 | (2006.01) |
| C07C 1/02 | (2006.01) |
| C07C 27/00 | (2006.01) |
| C10J 3/46 | (2006.01) |

(52) U.S. Cl. ............... 48/197 R; 48/201; 48/197 FM; 48/199 FM; 423/650; 423/651; 423/652; 423/220; 423/242.1; 423/352; 518/700; 252/373

(58) Field of Classification Search ............... 48/201, 48/197 FM, 197 R, 199 FM; 423/650, 651, 423/652, 220, 352, 242.1; 518/700; 252/373
See application file for complete search history.

(56) References Cited

U.S. PATENT DOCUMENTS

| | | | |
|---|---|---|---|
| 604,330 | A | 5/1898 | Kibling |
| 1,520,737 | A | 12/1924 | Wright |
| 1,634,236 | A | 6/1927 | Ranney |
| 1,660,187 | A | 2/1928 | Ehrat |
| 1,660,818 | A | 2/1928 | Leo |
| 1,722,679 | A | 7/1929 | Ranney |
| 1,936,643 | A | 10/1929 | Reed |
| 1,735,012 | A | 11/1929 | Rich |
| 1,735,481 | A | 11/1929 | Uren |
| 1,811,560 | A | 6/1931 | Ranney |
| 1,816,260 | A | 7/1931 | Lee |
| 1,852,717 | A | 4/1932 | Grinnell et al. |
| 1,884,859 | A | 10/1932 | Ranney |
| 1,910,762 | A | 5/1933 | Grinnell et al. |

(Continued)

FOREIGN PATENT DOCUMENTS

CA    986146    3/1976

(Continued)

OTHER PUBLICATIONS

U.S. Appl. No. 12/237,163, filed Sep. 24, 2008, Gil.

(Continued)

*Primary Examiner* — Timothy Vanoy

(74) *Attorney, Agent, or Firm* — Sheridan Ross P.C.

(57) ABSTRACT

The present invention, in one configuration, is directed to producing a methane-containing gas from a hydrocarbon fuel energy source extracted from an in-situ recovery operation, such as a SAGD or HAGD operation, and subsequently converting at least a portion of the gas into steam, electrical power and diluents for subsequent use in the aforementioned in-situ recovery operation while emitting only controlled amounts of carbon dioxide into the environment.

21 Claims, 3 Drawing Sheets

U.S. PATENT DOCUMENTS

| | | | |
|---|---|---|---|
| 2,148,327 A | 2/1939 | Smith et al. |
| 2,193,219 A | 3/1940 | Bowie et al. |
| 2,200,665 A | 5/1940 | Bolton |
| 2,210,582 A | 8/1940 | Grosse et al. |
| 2,365,591 A | 12/1944 | Ranney |
| 2,670,801 A | 3/1954 | Sherborne |
| 2,783,986 A | 3/1957 | Nelson et al. |
| 2,786,660 A | 3/1957 | Alleman |
| 2,799,641 A | 7/1957 | Bell |
| 2,823,752 A | 2/1958 | Hellmuth |
| 2,857,002 A | 10/1958 | Pevere et al. |
| 2,888,987 A | 6/1959 | Parker |
| 2,914,124 A | 11/1959 | Ripley, Jr. |
| 2,989,294 A | 6/1961 | Coker |
| 3,017,168 A | 1/1962 | Carr |
| 3,024,013 A | 3/1962 | Rogers et al. |
| 3,034,773 A | 5/1962 | Legatski |
| 3,207,221 A | 9/1965 | Cochran et al. |
| 3,227,229 A | 1/1966 | Wakefield, Jr. |
| 3,259,186 A | 7/1966 | Dietz |
| 3,285,335 A | 11/1966 | Reistle, Jr. |
| 3,333,637 A | 8/1967 | Prats |
| 3,338,306 A | 8/1967 | Cook |
| 3,353,602 A | 11/1967 | Geertsma |
| 3,362,751 A | 1/1968 | Tinlin |
| 3,386,508 A | 6/1968 | Bielstein et al. |
| 3,455,392 A | 7/1969 | Prats |
| 3,456,730 A | 7/1969 | Lange |
| 3,474,863 A | 10/1969 | Deans et al. |
| 3,530,939 A | 9/1970 | Turner et al. |
| 3,613,806 A | 10/1971 | Malott |
| 3,620,313 A | 11/1971 | Elmore et al. |
| 3,678,694 A | 7/1972 | Haspert |
| 3,759,575 A | 9/1973 | Boyd et al. |
| 3,768,559 A | 10/1973 | Allen et al. |
| 3,778,107 A | 12/1973 | Haspert |
| 3,784,257 A | 1/1974 | Lauber et al. |
| 3,833,059 A | 9/1974 | Sisson |
| 3,838,738 A | 10/1974 | Redford et al. |
| 3,882,941 A | 5/1975 | Pelofsky |
| 3,884,261 A | 5/1975 | Clynch |
| 3,888,543 A | 6/1975 | Johns |
| 3,922,148 A | 11/1975 | Child |
| 3,922,287 A | 11/1975 | Pawson et al. |
| 3,924,895 A | 12/1975 | Leasure |
| 3,937,025 A | 2/1976 | Alverez-Calderone |
| 3,941,423 A | 3/1976 | Garte |
| 3,946,810 A | 3/1976 | Barry |
| 3,948,323 A | 4/1976 | Sperry et al. |
| 3,954,140 A | 5/1976 | Hendrick |
| 3,960,408 A | 6/1976 | Johns |
| 3,986,557 A | 10/1976 | Striegler et al. |
| 3,992,287 A | 11/1976 | Rhys |
| 4,046,191 A | 9/1977 | Neath |
| 4,055,959 A | 11/1977 | Fritz |
| 4,064,942 A | 12/1977 | Prats |
| 4,067,616 A | 1/1978 | Smith et al. |
| 4,072,018 A | 2/1978 | Alvarez-Calderon |
| 4,076,311 A | 2/1978 | Johns |
| 4,085,803 A | 4/1978 | Butler |
| 4,099,388 A | 7/1978 | Husemann et al. |
| 4,099,570 A | 7/1978 | Vandergrift |
| 4,099,783 A | 7/1978 | Verty et al. |
| 4,106,562 A | 8/1978 | Barnes et al. |
| 4,116,487 A | 9/1978 | Yamazaki et al. |
| 4,144,935 A | 3/1979 | Bridges et al. |
| 4,149,597 A | 4/1979 | Redford et al. |
| 4,152,027 A | 5/1979 | Fujimoto et al. |
| 4,160,481 A | 7/1979 | Turk et al. |
| 4,165,903 A | 8/1979 | Cobbs |
| 4,167,290 A | 9/1979 | Yamazaki et al. |
| 4,203,626 A | 5/1980 | Hamburger |
| 4,209,268 A | 6/1980 | Fujiwara et al. |
| 4,216,999 A | 8/1980 | Hanson |
| 4,224,988 A | 9/1980 | Gibson et al. |
| 4,227,743 A | 10/1980 | Ruzin et al. |
| 4,236,640 A | 12/1980 | Knight |
| 4,249,777 A | 2/1981 | Morrell et al. |
| 4,257,650 A | 3/1981 | Allen |
| 4,265,307 A | 5/1981 | Elkins |
| 4,279,743 A | 7/1981 | Miller |
| 4,285,548 A | 8/1981 | Erickson |
| 4,289,354 A | 9/1981 | Zakiewicz |
| 4,296,969 A | 10/1981 | Willman |
| 4,406,499 A | 9/1983 | Yildirim |
| 4,410,216 A | 10/1983 | Allen |
| 4,434,849 A | 3/1984 | Allen |
| 4,440,449 A | 4/1984 | Sweeney |
| 4,445,723 A | 5/1984 | McQuade |
| 4,455,216 A | 6/1984 | Angevine et al. |
| 4,456,305 A | 6/1984 | Yoshikawa |
| 4,458,945 A | 7/1984 | Ayler et al. |
| 4,458,947 A | 7/1984 | Hopley et al. |
| 4,463,988 A | 8/1984 | Bouck et al. |
| 4,486,050 A | 12/1984 | Snyder |
| 4,494,799 A | 1/1985 | Snyder |
| 4,502,733 A | 3/1985 | Grubb |
| 4,505,516 A | 3/1985 | Shelton |
| 4,533,182 A | 8/1985 | Richards |
| 4,536,035 A | 8/1985 | Huffman et al. |
| 4,545,435 A | 10/1985 | Bridges et al. |
| 4,566,961 A | 1/1986 | Diaz et al. |
| 4,575,280 A | 3/1986 | Hemphill et al. |
| 4,595,239 A | 6/1986 | Ayler et al. |
| 4,601,607 A | 7/1986 | Lehmann |
| 4,603,909 A | 8/1986 | LeJeune |
| 4,607,888 A | 8/1986 | Trent et al. |
| 4,607,889 A | 8/1986 | Hagimoto et al. |
| 4,611,855 A | 9/1986 | Richards |
| 4,682,471 A | 7/1987 | Wagner |
| 4,699,709 A | 10/1987 | Peck |
| 4,753,666 A | 6/1988 | Pastor et al. |
| 4,774,470 A | 9/1988 | Takigawa et al. |
| 4,793,736 A | 12/1988 | Thompson et al. |
| 4,808,030 A | 2/1989 | Takegawa |
| 4,856,936 A | 8/1989 | Hentschel et al. |
| 4,911,578 A | 3/1990 | Babendererde |
| 4,946,579 A | 8/1990 | Occelli |
| 4,946,597 A | 8/1990 | Sury |
| 4,983,077 A | 1/1991 | Sorge et al. |
| 5,016,710 A | 5/1991 | Renard et al. |
| 5,032,039 A | 7/1991 | Hagimoto et al. |
| 5,051,033 A | 9/1991 | Grotenhofer |
| 5,125,719 A | 6/1992 | Snyder |
| 5,141,363 A | 8/1992 | Stephens |
| 5,174,683 A | 12/1992 | Grandori |
| 5,205,613 A | 4/1993 | Brown, Jr. |
| 5,211,510 A | 5/1993 | Kimura et al. |
| 5,217,076 A | 6/1993 | Masek |
| 5,280,814 A | 1/1994 | Stroh |
| 5,316,664 A | 5/1994 | Gregoli et al. |
| 5,330,292 A | 7/1994 | Sakanishi et al. |
| 5,339,898 A | 8/1994 | Yu et al. |
| 5,354,359 A | 10/1994 | Wan et al. |
| 5,446,980 A | 9/1995 | Rocke |
| 5,484,232 A | 1/1996 | Hayashi et al. |
| 5,516,967 A | 5/1996 | Pandey et al. |
| 5,534,136 A | 7/1996 | Rosenbloom |
| 5,534,137 A | 7/1996 | Griggs et al. |
| 5,626,726 A | 5/1997 | Kong et al. |
| 5,655,605 A | 8/1997 | Matthews |
| 5,656,136 A | 8/1997 | Gayaut et al. |
| 5,697,676 A | 12/1997 | Kashima et al. |
| 5,767,680 A | 6/1998 | Torres-Verdin et al. |
| 5,785,736 A | 7/1998 | Thomas et al. |
| 5,831,934 A | 11/1998 | Gill et al. |
| 5,852,262 A | 12/1998 | Gill et al. |
| 5,879,057 A | 3/1999 | Schwoebel et al. |
| 5,890,771 A | 4/1999 | Cass |
| 6,003,953 A | 12/1999 | Huang et al. |
| 6,017,095 A | 1/2000 | DiMillo |
| 6,027,175 A | 2/2000 | Seear et al. |
| 6,190,536 B1 | 2/2001 | Lokhandwala et al. |
| 6,206,478 B1 | 3/2001 | Uehara et al. |
| 6,257,334 B1 | 7/2001 | Cyr et al. |
| 6,263,965 B1 | 7/2001 | Schmidt et al. |
| 6,277,286 B1 | 8/2001 | Søntvedt et al. |

| | | | |
|---|---|---|---|
| 6,364,418 | B1 | 4/2002 | Schwoebel |
| 6,399,030 | B1 | 6/2002 | Nolan |
| 6,412,555 | B1 | 7/2002 | Sten-Halvorsen et al. |
| 6,554,368 | B2 | 4/2003 | Drake et al. |
| 6,569,235 | B2 | 5/2003 | Carter, Jr. |
| 6,604,580 | B2 | 8/2003 | Zupanick et al. |
| 6,631,761 | B2 | 10/2003 | Yuan et al. |
| 6,679,326 | B2 | 1/2004 | Zakiewicz |
| 6,758,289 | B2 | 7/2004 | Kelley et al. |
| 6,767,518 | B2 * | 7/2004 | Ichikawa et al. .............. 48/61 |
| 6,796,381 | B2 | 9/2004 | Ayler et al. |
| 6,857,487 | B2 | 2/2005 | Galloway et al. |
| 6,869,147 | B2 | 3/2005 | Drake et al. |
| 6,880,633 | B2 | 4/2005 | Wellington et al. |
| 6,890,497 | B2 | 5/2005 | Rau et al. |
| 6,929,330 | B2 | 8/2005 | Drake et al. |
| 6,948,562 | B2 | 9/2005 | Wellington et al. |
| 6,997,256 | B2 | 2/2006 | Williams et al. |
| 7,066,254 | B2 | 6/2006 | Vinegar et al. |
| 7,066,973 | B1 | 6/2006 | Bentley |
| 7,097,255 | B2 | 8/2006 | Drake et al. |
| 7,128,375 | B2 | 10/2006 | Watson |
| 7,185,707 | B1 | 3/2007 | Graham |
| 7,192,092 | B2 | 3/2007 | Watson |
| 7,240,730 | B2 | 7/2007 | Williams et al. |
| 7,264,788 | B2 | 9/2007 | Hampden-Smith et al. |
| 7,381,320 | B2 | 6/2008 | Iqbal et al. |
| 7,428,926 | B2 | 9/2008 | Heins |
| 7,448,692 | B2 | 11/2008 | Drake et al. |
| 7,461,901 | B2 | 12/2008 | Drake et al. |
| 7,691,788 | B2 | 4/2010 | Tan et al. |
| 2002/0143693 | A1 | 10/2002 | Soestbergen et al. |
| 2003/0146002 | A1 | 8/2003 | Vinegar et al. |
| 2003/0188863 | A1 | 10/2003 | Gilbert et al. |
| 2004/0211559 | A1 | 10/2004 | Nguyen et al. |
| 2004/0249732 | A1 | 12/2004 | Drummond |
| 2005/0051362 | A1 | 3/2005 | McGuire et al. |
| 2006/0231455 | A1 | 10/2006 | Olsvik et al. |
| 2007/0039729 | A1 | 2/2007 | Watson |
| 2007/0044957 | A1 | 3/2007 | Watson |
| 2007/0181083 | A1 | 8/2007 | Fulton et al. |
| 2007/0237696 | A1 | 10/2007 | Payton |
| 2007/0277438 | A1 | 12/2007 | Lynch et al. |
| 2008/0017416 | A1 | 1/2008 | Watson et al. |
| 2008/0078552 | A1 | 4/2008 | Donnelly et al. |
| 2008/0087422 | A1 | 4/2008 | Kobler et al. |
| 2008/0122286 | A1 | 5/2008 | Brock et al. |
| 2008/0308174 | A1 | 12/2008 | Huglen |

FOREIGN PATENT DOCUMENTS

| | | |
|---|---|---|
| CA | 986544 | 3/1976 |
| CA | 1165712 | 4/1984 |
| CA | 1167238 | 5/1984 |
| CA | 1224911 | 8/1987 |
| CA | 2124199 | 6/1992 |
| CA | 2222668 | 5/1998 |
| CA | 2340506 | 9/2001 |
| CA | 2526854 | 9/2001 |
| CA | 2583508 | 9/2001 |
| CA | 2583513 | 9/2001 |
| CA | 2583519 | 9/2001 |
| CA | 2583523 | 9/2001 |
| CA | 2358805 | 10/2001 |
| CA | 2315596 | 2/2002 |
| CA | 2332207 | 2/2002 |
| EP | 0120625 | 10/1986 |
| JP | 03-267497 | 11/1991 |
| WO | WO 01/69042 | 9/2001 |
| WO | WO 2007/133461 | 11/2007 |
| WO | WO 2008/051822 | 5/2008 |
| WO | WO 2008/131169 | 10/2008 |
| WO | WO 2008/138118 | 11/2008 |

OTHER PUBLICATIONS

U.S. Appl. No. 12/327,547, filed Dec. 3, 2008, Brock, et al.

U.S. Appl. No. 12/366,845, filed Feb. 6, 2009, Gil, et al.

Nasr, "Steam Assisted Gravity Drainage (SAGD): A New Oil Production Technology for Heavy Oil and Bitumens", CSEG Recorder, Alberta Research Council, Calgary, Canada, Mar. 2003, p. 42.

Huang, et al., "Wet Electric Heating for Starting Up SAGD/VAPEX", Alberta Research Council, Presented at the Petroleum Society's 5th Canadian International Petroleum Conference, Jun. 2004, pp. 1-12, Paper 2004-130, Petroleum Society: Canadian Institute of Mining, Metallurgy and Petroleum.

Hardy, "Feasibility Study for Underground Mining of Oil Sand", Department of Energy, Mines and Resources, Canada, Sep. 1977, pp. 1-314.

Harris, et al., "Feasibility of Underground Mining of Oil Sand", Alberta Oil Sands Information Center, 1978, pp. 1-33.

O'Rourke, et al., "AOSTRA's Underground Test Facility (UTF): Mine-Assisted Recovery Under Difficult Conditions", CIM Bulletin, Jan. 1989, pages unknown, vol. 82., No. 921.

Stephenson et al., "Mining Aspects Of Hard To Access Oil Sands Deposits", Norwest Corporation, Mar. 2, 2006, pp. 1-57.

Deutsch et al., "Guide To SAGD (Steam Assisted Gravity Drainage) Reservoir Characterization Using Geostatistics", Centre for Computational Geostatistics (CCG) Guidebook Series vol. 3, 2005 (27 pages).

Author Unknown, "Technical Overview: Nigeria's Bitumen Belt and Developmental Potential", Ministry of Solid Minerals Development, Mar. 6, 2006, Available at http://64.233.167.104/search?q_cache:m12yiQ5o16EJ:msmd.gov.ng/privatisation/docs/Bitumen%2520Overview.pdf+SAGD+a..., printed Jan. 10, 2007, pp. 1-48.

Piper, et al., "An Evaluation of Heavy Oil Mining", Energy Development Consultants,, Inc. and Stone Webster Engineering Corp., Department of Energy Contract No. DE-AC03-80PC30259, Dec. 1982, pp. 1-270.

Hutchins, et al., "Mining for Petroleum: Feasibility Study", Energy Development Consultants, Inc., US Bureau of Mines Contract No. JO275002, Jul. 1978, pp. 1-365.

Author Unknown, "Future of Oil Recovery from Underground Drill Sites", Underground Technology Research Council, Committee of Mine Assisted Oil Recovery, Dec. 1988, pp. 1-51.

Fontaine, et al., "An Evaluation of Oil Mining in Ohio Phase II", Sep. 1983, pp. 1-58.

Fontaine, et al., "Recommended Reservoir Engineering Testing Program for Oil Mining Projects", Jan. 1984, pp. 1-140.

Riddell, "Oil Mining A Review of Projects", Jun. 1984, pp. 1-32.

Hutchins, et al., "Oil Mining: An Emerging Technology", Wassum Mining Engineering, Dec. 1981, pp. 1-4.

Dick, et al., "Oil Mining", U.S. Bureau of Mines, 1980, pp. 1-6.

Dobson, et al., "Mining Technology Assists Oil Recovery from Wyoming Field", Journal of Petroleum Technology, from Soc. Pet Eng., Apr. 1981, pp. 1-7.

Author Unknown, "Oil Mining: The Fourth Order of Oil Recovery", Compressed Air Magazine, Dec. 1983, pp. 6-10.

Riddell, et al., "Heavy Oil Mining Technical and Economic Analysis", Presented at California Regional Meeting of the Society of Petroleum Engineers, Long Beach, CA Apr. 11-13, 1984, pp. 1-24.

Mikula et al., "Oil Sands Conditioning, Bitumen Release Mechanisms, and New Process Development", Alberta Oil Sands Information Services, 1999, pp. 1-8.

Mikula et al., "Commercial Implementation of a Dry Landscape Oil Sands Tailings Reclamation Option: Consolidated Tailings", Alberta Oil Sands Information Services; No. 1998.096, date unknown, pp. 907-921.

Czarnecki, Press Release; NSERC Industrial Research Chair in Oil Sands Syncrude Canada, Ltd, date unknown, pp. 1-3.

Canadian Heavy Oil Associate (CHOA) Annual Conference, Dec. 6, 2000, presentation by Oil Sands Underground Mining, Inc.

Corti, et al., "Athabasca Mineable Oil Sands: The RTR/Gulf Extraction Process Theoretical Model of Bitumen Detachment," The 4.sup.th UNITAR/UNDP International Conference on Heavy Crude and Tar Sands Proceedings, vol. 5, Edmonton, AB, Aug. 7-12, 1988, pp. 41-44, 71.

Author Unknown, "Underground Mining of Oil Sands," Oil Sands Underground Mining, Inc., presented at National Oil Sands Task Force, Jan. 2001 Quarterly Meeting, pp. 1-38.

Author Unknown, "A New Technology for the Recovery of Oil Sands," Oil Sands Underground Mining, Inc., presented at combined Oil Sands Task Force and Black Oil Pipeline Network Meeting, Jun. 2001, pp. 1-30.

Oil Sands Underground Mining, Inc., "A Private Sector Approach to Design/Build," presented at NAT 2002, 34 pages.

Drake, et al., "A Promising New Concept for Underground Mining of Oil Sands," technical papers presented to Canadian Institute of Mining (CIM), Ft. McMurray, Jun. 13-15, 2001, pp. 1-16.

Drake, "An Innovative Approach for the Underground Mining of Oil Sands," presented at North American Tunneling 2002, Seattle, WA May 2002 and NARMS-TAC 202, Mining and Tunneling Innovation and Opportunity Conference, Toronto, Ontario, Jul. 2002, pp. 1-8.

Butler, "Thermal Recovery of Oil and Bitumen", 2nd Printing by GravDrain, Inc., Calgary, Alberta,1998, Parts 1-8, pp. 1-548.

Li, et al., "Prediction of Oil Production by Gravity Drainage", Stanford University, SPE 84 184, Oct. 2003, pp. 1-8.

"Plan of Operation, Shell Frontier Oil and Gas Inc., E-ICP Test Project", Oil Shale Research and Development Project, Prepared for Bureau of Land Management, Feb. 15, 2006, pp. 1-70.

Sahni, et al., "Electromagnetic Heating Methods for Heavy Oil Reservoirs", Submitted to 2000 Society of Petroleum Engineers, SPE/AAPG Western Regional Meeting, May 1, 2000, Long Beach, CA, pp. 1-12.

International Preliminary Report on Patentability for International (PCT) Application No. PCT/IB2008/003846, mailed Mar. 24, 2011.

U.S. Appl. No. 12/782,293, filed May 18, 2010, Donnelly et al.

"Vektron® 6913 $No_x$ Reduction Strategy Implementation Options," Infineum International Ltd., 2000, online: US EPA http://www.epa.gov.otaq.regs/fuels/additive/i-b-03b.pdf.

Haefeli et al., "Carbon Dioxide Capture and Storage Issues—Accounting and Baselines Under the United Nations Framework Convention on Climate Change (UNFCCC)," International Energy Agency, Paris, May 2004.

U.S. Appl. No. 12/469,374, filed May 20, 2009, Gil, et al.

U.S. Appl. No. 12/498,895, filed Jul. 7, 2009, Gil, et al.

"Carbon Sequestration Atlas of the United States and Canada", U.S. Department of Energy, Office of Fossil Energy, National Energy Technology Laboratory, Mar. 2007, available at http://www.netl.doe.gov/technologies/carbon_seq/refshelf/atlas/ATLAS.pdf, pp. 1-90.

"Liquefied Petroleum Gas" and "Natural Gas", Handbook of Fuels, 2008, Wiley-VCH Verlag GmbH & Co. KgaA, edited by Barbara Elvers, pp. 140-141 and 152-154.

Gallucci, et al., "SEM Analysis Application to Study CO2 Capture by Means of Dolomite", Open-Access Journal for the Basic Principles of Diffusion Theory, Experiment and Application, 2007, available at http://www.uni-leipzig.de/diffusion/journal/pdf/volume7/diff_fund_7(2007)5.pdf, pp. 1-11.

Schmidt, "What's new in production", World Oil, Oct. 2006, vol. 227, No. 10, p. 14, available at http://web.ebscohost.com.proxy.bib.uottawa.ca/ehost/delivery?vid=4&hid=105&sid=3ab.., accessed Jul. 16, 2009, pp. 1-3.

International Search Report for International (PCT) Application No. PCT/IB2008/003846, mailed Aug. 31, 2009.

Written Opinion for International (PCT) Application No. PCT/IB2008/003846, mailed Aug. 31, 2009.

Official Action for Canadian Patent Application No. 2,698,238, dated Aug. 24, 2011.

* cited by examiner

METHOD OF REMOVING CARBON DIOXIDE EMISSIONS FROM IN-SITU RECOVERY OF BITUMEN AND HEAVY OIL

CROSS REFERENCE TO RELATED APPLICATION

The present application claims the benefits, under 35 U.S.C. §119(e), of U.S. Provisional Application Ser. No. 60/981,724, filed Oct. 22, 2007, entitled "Method of Eliminating Carbon Dioxide from Thermal Recovery of Upgrading Bitumen and Heavy Oil" to Gil and U.S. Provisional Application Ser. No. 60/990,519, filed Nov. 27, 2007, entitled "Method of Eliminating Carbon Dioxide from Thermal Recovery of Upgrading Bitumen and Heavy Oil" to Gil, both of which are incorporated herein by this reference.

FIELD

The present invention relates generally to a method and means of providing high quality synthetic natural gas ("NG") fuel, electrical power and diluents to an in-situ recovery operation such as for example SAGD or HAGD using a hydrocarbon fuel energy source but emitting no significant carbon dioxide during the hydrocarbon recovery operation.

BACKGROUND

Oil is a nonrenewable natural resource having great importance to the industrialized world. The increased demand for and decreasing supplies of conventional oil has led to the development of alternate sources of oil such as deposits of bitumen and heavy crude as well as a search for more efficient methods for recovering and processing hydrocarbons extracted from such deposits.

There are substantial deposits of oil sands in the world, with particularly large deposits in Canada and Venezuela. For example, the Athabasca oil sands region of the Western Canadian Sedimentary Basin contains an estimated 1.3 trillion barrels of potentially recoverable bitumen. An equally large deposit of bitumen may be found in the Carbonates of Alberta. There are lesser, but significant deposits, found in the U.S. and other countries. These oil sands and carbonate reservoirs contain a petroleum substance called bitumen or heavy oil. Bitumen deposits cannot be economically exploited by traditional oil well technology because the bitumen or heavy oil is too viscous to flow at natural reservoir temperatures.

When oil sand deposits are near the surface, they can be economically recovered by surface mining methods. The current principal method of bitumen recovery, for example, in the Alberta oil sands is by conventional surface mining of shallower deposits using large power shovels and trucks to feed a nearby slurry conversion facility which is connected to a primary bitumen extraction facility by a long hydrotransport haulage system. The bitumen is finally taken to an upgrader facility where it is refined and converted into crude oil and other petroleum products.

When oil sand deposits are too far below the surface for economic recovery by surface mining, bitumen can be economically recovered in many, but not all, areas by recently developed in-situ recovery methods, such as Steam Assisted Gravity Drain ("SAGD"), VAPEX, and other variants of gravity drainage technology to mobilize the bitumen or heavy oil. The principal method currently being implemented on a large scale is SAGD. Typically, SAGD wells, or well pairs, are drilled from the earth's surface down to the bottom of the oil sand deposit and then horizontally along the bottom of the deposit. The wells inject steam to reduce the viscosity of bitumen. The wells then collect the mobilized bitumen.

Heat Assisted Gravity Drain ("HAGD") is a relatively new process for mobilizing bitumen in the Alberta oil sands and in carbonates. Electric heater elements are embedded in the reservoir material and used, in place of steam, to heat the formation until the bitumen becomes fluid enough to flow by gravity drain. HAGD may require more energy than SAGD but may be used in reservoirs where SAGD cannot—such as, for example, reservoirs with poor steam caps. HAGD and SAGD may also be used in combination, where HAGD elements are used to melt the bitumen around the steam injectors, thereby allowing the steam chamber to form more quickly. Solvents such as carbon dioxide and paraffins and/or olefins may also be used to help mobilize the bitumen or heavy oil such as for example in SAGD/HAGD and other solvent recovery operations or combinations thereof.

Because of global warming concerns, this potential for substantially increasing carbon dioxide emissions may outweigh the advantages of the enormous reserves of unconventional hydrocarbon deposits available.

Even the most efficient SAGD or HAGD operation requires substantial amounts of energy to deliver the required amount of steam or heat to the reservoir to mobilize the bitumen. If this energy is obtained by burning fossil fuels, there is the potential to generate significant amounts of carbon dioxide emissions during recovery operations. The thermal energy required to mobilize bitumen can be quantified by a Steam-Oil-Ratio ("SOR"), which is determined by the number of barrels of water required to produce the steam divided by the number of barrels of oil or bitumen recovered. In a SAGD operation having an average SOR of 3, the energy required to produce high quality steam to recover 1 barrel of heavy oil or bitumen oil is equivalent to about ¼ of a barrel of oil. Thus, oil produced by thermal recovery methods have the potential to generate 25% or more carbon dioxide emissions than oil recovered by pumping from conventional oil wells.

In addition, the upgrading process when carried out underground, such as described for example in U.S. Pat. No. 7,066,254 or at a surface refinery can generate additional carbon dioxide and other unwanted emissions.

There has been much effort to utilize all the on-site water and energy potential derived from a SAGD operation to increase the overall efficiency of the operation and to prepare the produced bitumen or heavy oil for pipeline transmission over existing pipeline networks.

There remains, therefore, a need for a method to eliminate carbon dioxide emissions generated during thermal recovery operations of unconventional oil such as heavy oils and bitumen. Further, there is a need to utilize any number of readily available fossil fuels to power thermal recovery operations while substantially reducing or eliminating carbon dioxide emissions.

SUMMARY

These and other needs are addressed by the present invention. The various embodiments and configurations of the present invention are directed generally to a process for using any number of readily available hydrocarbon fuels such as coal, bitumen, petroleum coke ("pet coke"), peat, kerogen, asphaltenes and the like, to generate a methane-containing gas, such as natural gas. The gas, in turn, can be used as a fuel source to generate steam, electrical power and/or diluents for in-situ recovery of heavy oil or bitumen. These processes can be designed to capture and sequester the preponderance of the carbon dioxide emissions from the various chemical and combustion processes within the overall processes. This substantial reduction or elimination of carbon dioxide emissions to the atmosphere can be important since it allows heavy oil or bitumen to be recovered by any in-situ method while not adding to fossil carbon dioxide emissions. This can allow the production of refined oil from the huge reserves of unconventional oil sources, such as heavy oil and bitumen from oil sands and carbonates, without adding additional carbon dioxide emissions.

The production of methane from any number of readily available fossil fuels can be a stand-alone process for generating natural gas and electrical power without atmospheric carbon dioxide emissions. A method is disclosed herein to produce methane for use in any number of applications, especially for generating steam and electrical power for SAGD and/or HAGD operations. The process includes provisions for controlling and sequestering most of the carbon dioxide generated during the process.

The use of methane to generate power for thermal recovery of heavy oil or bitumen can be a stand alone process for SAGD and/or HAGD operations without high atmospheric carbon dioxide emissions. Two embodiments of the processes using methane as a fuel source are disclosed. In the first, hydrogen is the fuel produced and used to generate steam and electrical power. In the second, ammonia is the fuel produced and used to generate steam and electrical power. The second embodiment also results in the production of diluents which can be used in SAGD, HAGD or other in-situ recovery operations for various purposes. Steam generation from waste heat and from reforming is salvaged and integrated into SAGD/HAGD processes.

Finally, the processes can be combined such that readily available, alternate fossil fuels such as coal, bitumen, pet coke can be used to produce methane, which, in turn, can be used to power SAGD, HAGD, solvent and other in-situ recovery operations without high atmospheric carbon dioxide emissions and to make paraffin and/or olefin diluents that can be added to the recovered bitumen to allow it to flow, for example, in pipelines.

The ability to use hydrocarbon fuels such as natural gas, syngas, coal, peat, kerogen, bitumen, pet coke or asphaltenes to recover heavy oil or bitumen reserves without significant atmospheric carbon dioxide emissions opens up the possibility of producing refined petroleum products, such as diesel, gasoline etc., on a roughly equal emissions footing with refined petroleum products originating from conventional light oil reservoirs. The use of these alternate fuel sources serve to improve the economic viability of SAGD, HAGD, solvent and other in-situ recovery operations.

The following definitions are used herein:

"A" or "an" entity refers to one or more of that entity. As such, the terms "a" (or "an"), "one or more" and "at least one" can be used interchangeably herein. It is also to be noted that the terms "comprising", "including", and "having" can be used interchangeably.

"At least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Asphaltenes are molecular substances found in crude oil, along with resins, aromatic hydrocarbons, and alkanes. Asphaltenes consist primarily of carbon, hydrogen, nitrogen, oxygen, and sulfur, as well as trace amounts of vanadium and nickel. The C:H ratio is approximately 1:1.2, depending on the asphaltene source. Asphaltenes are defined operationally as the n-heptane insoluble, toluene soluble component of a carbonaceous material such as crude oil, bitumen or coal.

Coal is a fossil fuel formed from plant remains by oxidization and biodegradation, thus sequestering atmospheric carbon. Coal is a combustible black or brownish-black rock. It is composed primarily of carbon and hydrogen along with small quantities of other elements, notably sulfur. Coal is extracted from the ground by either underground or surface coal mining.

A combined cycle gas turbine (CCGT) is a gas turbine generator that generates electricity, wherein the waste heat is used to make steam to generate additional electricity via a steam turbine. This last step enhances the efficiency of electricity generation.

The Fluid Catalytic Cracking process or FCC produces a high yield of gasoline and Liquid Petroleum Gas or LPG. As will be appreciated, hydrocracking is a major source of jet fuel, diesel, naphtha and LPG. Thermal cracking is currently used to upgrade very heavy fractions, or to produce light fractions or distillates, burner fuel and/or petroleum coke. Two extremes of the thermal cracking in terms of product range are represented by the high-temperature process called steam cracking or pyrolysis (ca. 750 to 900° C. or more) which produces valuable ethylene and other feed stocks for the petrochemical industry, and the milder-temperature delayed coking (ca. 500° C.) which can produce, under the right conditions, valuable needle coke, a highly crystalline petroleum coke used in the production of electrodes for the steel and aluminum industries.

A Heat Recovery Steam Generator or HRSG is a heat exchanger that recovers heat from a hot gas stream. It produces steam that can be used in a process or used to drive a steam turbine. A common application for an HRSG is in a combined-cycle power station, where hot exhaust from a gas turbine is fed to an HRSG to generate steam which in turn drives a steam turbine. This combination produces electricity more efficiently than either the gas turbine or steam turbine alone. The HRSG is also an important component in cogeneration plants. Cogeneration plants typically have a higher overall efficiency in comparison to a combined cycle plant. This is due to the loss of energy associated with the steam turbine.

A mobilized hydrocarbon is a hydrocarbon that has been made flowable by some means. For example, some heavy oils and bitumen may be mobilized by heating them or mixing them with a diluent to reduce their viscosities and allow them to flow under the prevailing drive pressure. Most liquid hydrocarbons may be mobilized by increasing the drive pressure on them, for example by water or gas floods, so that they can overcome interfacial and/or surface tensions and begin to flow.

An olefin diluent is diluent made from any of a series of unsaturated open-chain hydrocarbons corresponding in composition to the general formula $C_nH_{2n}$.

A paraffin is a saturated hydrocarbon with the general formula $C_nH_{2n+2}$. For n<5 (methane, ethane, propane and butane), the paraffins are gaseous at normal temperatures and pressures. For n=5 or greater, the paraffins are liquid or solid at normal temperatures and pressures. Paraffins are often called alkanes.

Peat is an accumulation of partially decayed vegetation matter and forms in wetlands or peatlands. Peat is composed mainly of marshland vegetation as well as other types of organic remains. Most modern peat bogs formed in high latitudes after the retreat of the glaciers at the end of the last ice age.

Petroleum coke or pet coke is a fuel produced using the byproducts of the petroleum refining process. When crude oil is refined to produce gasoline and other products, a residue is left over from this process that can be further refined by "coking" it at high temperatures and under great pressure. The resulting product is pet coke, a hard substance that is similar to coal. Pet coke has a higher heating value than coal, at around 14,000 Btu per pound, compared with 12,500 Btu per pound for coal.

Primary production or recovery is the first stage of hydrocarbon production, in which natural reservoir energy, such as gasdrive, waterdrive or gravity drainage, displaces hydrocarbons from the reservoir, into the wellbore and up to surface. Production using an artificial lift system, such as a rod pump, an electrical submersible pump or a gas-lift installation is considered primary recovery. Secondary production or recovery methods frequently involve an artificial-lift system and/or reservoir injection for pressure maintenance. The purpose of secondary recovery is to maintain reservoir pressure and to displace hydrocarbons toward the wellbore. Tertiary production or recovery is the third stage of hydrocarbon production during which sophisticated techniques that alter the original properties of the oil are used. Enhanced oil recovery can begin after a secondary recovery process or at any time during the productive life of an oil reservoir. Its purpose is not only to restore formation pressure, but also to improve oil displacement or fluid flow in the reservoir. The three major types of enhanced oil recovery operations are chemical flooding, miscible displacement and thermal recovery.

It is also understood that a reference to oil herein is intended to include low API hydrocarbons such as bitumen (API less than ~10°) and heavy crude oils (API from ~10° to ~20°) as well as higher API hydrocarbons such as medium crude oils (API from ~20° to ~35°) and light crude oils (API higher than ~35°).

DETAILED DESCRIPTION

There are several methods to recover bitumen or heavy oil from an oil sands deposit. It is understood that a reference to bitumen hereafter is intended to include heavy oil. These are:
 SAGD which uses steam to mobilize the bitumen and produces a mixture of hot bitumen and substantial water;
 HAGD which uses heat to mobilize the bitumen and produces a mixture of hot bitumen and some water;
 VAPEX and other solvent-based methods which uses a diluent to mobilize the bitumen and produces a mixture of cold bitumen, diluent and some water
 mechanically excavating which is a mining process typically producing an oil sand slurry. There are known processes to de-sand the slurry to produce a mixture of cold bitumen, and water; and
 hydraulic mining which uses pressurized water to fragment the oil sand and produces an oil sand slurry. There are known processes to de-sand the slurry to produce a mixture of cold bitumen, and substantial water.

In any of the above recovery processes, a mixture of bitumen, water and gases is recovered and can be further processed by the process of the present invention. All of the above processes can be carried out in-situ. Hydraulic mining, for example, can be accomplished in-situ from wells installed in the reservoir as described in U.S. patent application Ser. No. 11/944,013 entitled "Recovery of Bitumen by Hydraulic Excavation", filed 21 Nov. 2007.

To illustrate the process of the present invention, an example of a relatively large SAGD or HAGD operation is used for illustration. As can be appreciated, the process of the present invention can be applied to all the above methods of bitumen recovery. Only the relative amounts of water produced and the requirements for a mobilizing agent (such as steam for SAGD or diluent for VAPEX) are different.

Hydrocarbon Fuels Used to Make Methane

Figure 1:
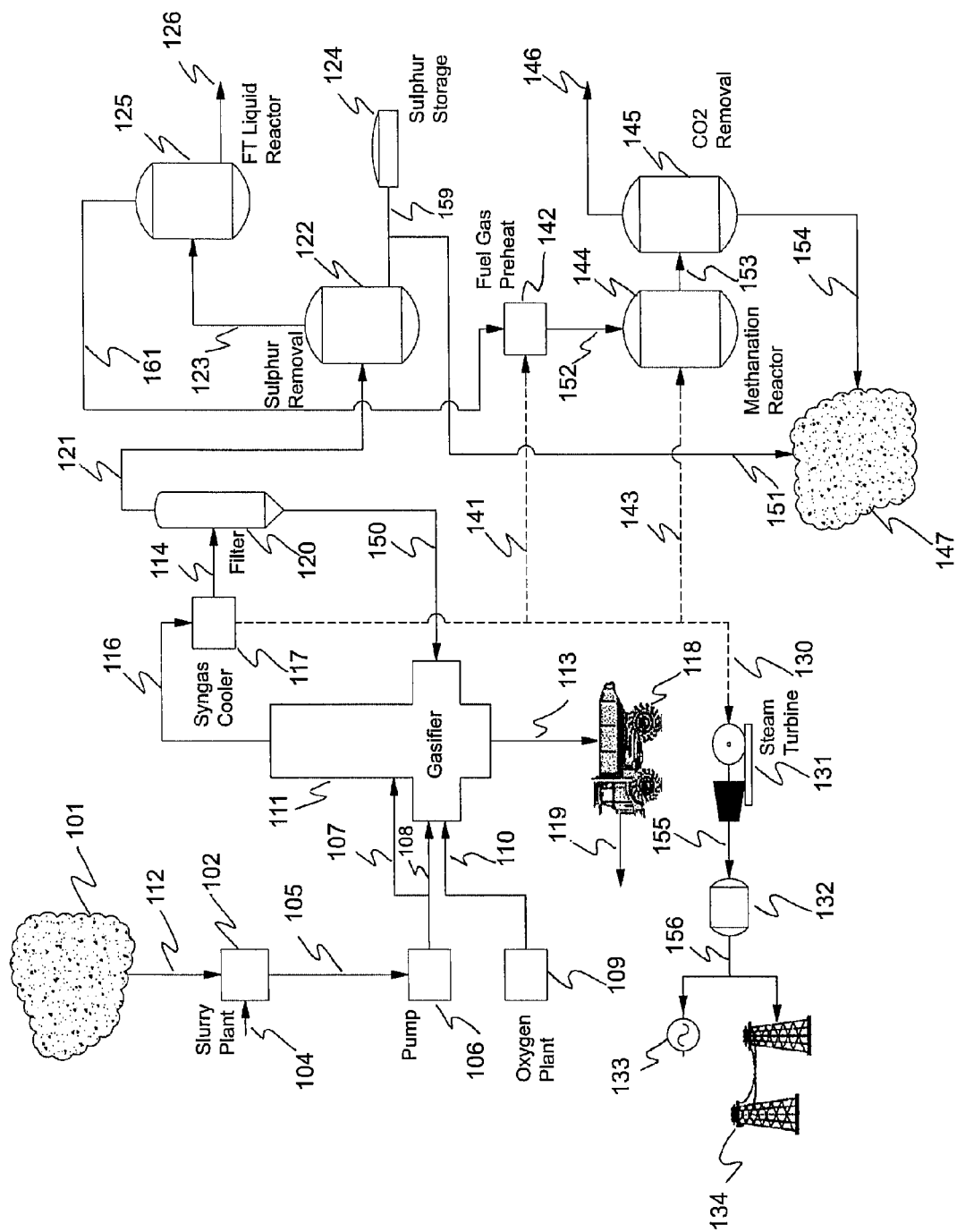
FIG. 1 is a schematic of a flow process for using a fossil fuel to produce natural gas.

FIG. 1 is a schematic of a flow process for using a readily available fuels such as coal, bitumen, pet coke, peat, and the like, to generate natural gas for use as a power source and to produce olefin and/or paraffin liquids for use as diluents in the production and transportation of bitumen (oil sands), kerogen (oil shale), heavy oil, and other fossil fuel sources. This can be a stand-alone process for generating natural gas and electrical power. Alternately, this process can be the first stage in a combined process to generate natural gas from any of a number of other hydrocarbon fuels and then use the natural gas to operate a SAGD or HAGD or combined SAGD/HAGD or other in-situ recovery operation such as described below in FIGS. 2 and 3. In all the processes described herein, the carbon dioxide generated may be sequestered underground and/or used for enhanced oil recovery ("EOR") purposes.

It is understood that hydrocarbon fuels as used below refer to fossil fuels such as coal, bitumen, pet coke, and the like as well as to fuels, such as for example peat, which is not strictly a fossil fuel but has been buried for only hundreds or thousands of years. Hydrocarbon fuels as used below also refer to other fuels such as asphaltenes which may be generated as part of an upgrading process.

In FIG. 1, a hydrocarbon fuel source 101, such as coal, pet coke, peat, or bitumen, is delivered via path 112 to a facility where it is converted to a slurry in apparatus 102. In addition to the hydrocarbon fuel source 101, water 104 is input to the slurry apparatus 102 and a hydrocarbon fuel slurry 105 is the output. An oxygen plant 109 delivers oxygen via path 110 to a gasifier apparatus 111. Fuel slurry is pumped via apparatus 106 into the first stage of gasifier 111 in via path 108 and into the second stage of gasifier 111 via path 107.

The gasification process produces a residual slag and a synthesized gas ("syngas"). The residual slag includes byproduct metals, such as nickel, vanadium and other trace metals, and the syngas various gas components, such as methane, ethane, propane, butane, pentane, carbon dioxide, carbon monoxide, molecular hydrogen, water vapor, and hydrogen sulfide. The predominant materials in the residual slag are carbon, nickel, vanadium with other residuals depending on the composition of the feed material. A typical syngas includes from about 10 to about 30 mole percent methane, from about 5 to about 10 mole percent hydrocarbons other than methane, from about 20 to about 50 mole percent molecular hydrogen, and from about 20 to about 50 mole percent carbon oxides (both carbon dioxide and monoxide), with the remainder being other components, such as hydrogen sulfide, sulphur dioxide, water vapor, and carbonil. As will be appreciated, gasification may be performed by any suitable technique. The products of gasification are dependent on the composition of the fuel source and the operating parameters of the gasifier.

When quenched by water, the slag is then sent via path 113 to, for example, a truck 118 and may be sold as a by-product 119 for metals recovery, for example.

The syngas is sent via path 116 to a syngas cooler apparatus 117, such as a heat exchanger, in which the syngas is in thermal contact or engagement with a water stream. The syngas cooler 117 transfers thermal energy from the syngas to the water, thereby generating steam, which is sent via path 130 and used to power a steam turbine 131. The steam turbine 131, in turn, provides power via path 155 to a generator 132 which provides electrical energy via path 156 that may be used to power on-site thermal recovery operations 133, other thermal recovery facilities 133 for consumption or sold to a power grid via transmission lines 134. Steam from syngas cooler 117 is also sent via path 141 to a fuel gas pre-heat apparatus 142 and via path 143 to methanation reactors 144 to concentrate carbon oxides and hydrogen into methane.

The syngas cooled in apparatus 117 is sent via path 114 to a filter apparatus 120 or other suitable unit to remove at least most of the particulate matter. The particulate matter is returned via path 150 to the first stage of the gasifier 111 for disposal.

The filtered syngas is then transferred via path 121 to a sulfur removal apparatus 122 to produce a treated synthesized gas containing at least most of the hydrocarbons and carbon oxides in the syngas and a waste gas comprising at least most of the sulfur compounds in the syngas. The sulfur compounds outputted by the apparatus 122 as the waste gas is sent via path 159 to a liquid sulfur storage tank 124, where it can be sold as a refined sulphur product, or sent via path 151 to be sequestered in an appropriate deep saline aquifer 147 or, optionally, used as a part of an EOR scheme. De-sulfurization may be realized by any suitable techniques.

The de-sulfurized or treated syngas is transferred from apparatus 122 via path 123 to a Fischer-Tropsch ("FT") liquid reactor or other liquification process 125. In the liquification reactor 125, at least most of the methane and ethane in the treated syngas are converted into natural gas liquids ("NGL"), such as propane $C_3H_8$, n-butane $C_4H_{10}$ and n-pentane $C_5H_{12}$. The NGLs can be sold as by-products 126 or used as diluents for transporting recovered and cleaned bitumen from a SAGD or HAGD thermal recovery operation to a refinery. Other processes such as synthetic natural gas to methanol and methanol to olefins may be used in lieu of the FT process.

The remaining gaseous fuels from the FT reactor 125 (primarily methane, carbon dioxide, ethane and hydrogen) are transferred via path 161 to a fuel gas pre-heat apparatus 142 where a portion of the steam generated in syngas cooler apparatus 117 is added via path 141. The resultant gas is then transferred via path 152 to one or more methanation reactors 144 where additional steam generated in syngas cooler apparatus 117 is added via path 143. The methanation product gas, or output of the methanation reactors 144, includes, as gas components, primarily methane and carbon dioxide. Although methanation is discussed as an example, other techniques for converting hydrocarbons and carbon oxides into methane are also considered.

The product gas is transferred via path 153 to a carbon dioxide removal and recovery apparatus 145, which forms an output gas including at least most of the hydrocarbons in the product gas and a second waste gas including at least most of the carbon oxides in the product gas. Carbon oxide removal may be accomplished by any suitable techniques, such as, for example, alcohol-based absorbent techniques. The recovered carbon dioxide in the second waste gas is then injected via path 154 into an underground reservoir 147 for sequestration. The underground reservoir 147 may be a producing reservoir, an overlying gas cap, a geologic formation not connected with the producing reservoir, or the like. Once sequestered, the $CO_2$ may be used for enhanced oil recovery ("EOR") operations. As can be appreciated, the $CO_2$ can be delivered directly to EOR operations from the carbon dioxide capture apparatus 145. As noted previously, the technology for $CO_2$ injection and EOR are proven processes.

Figure 2:
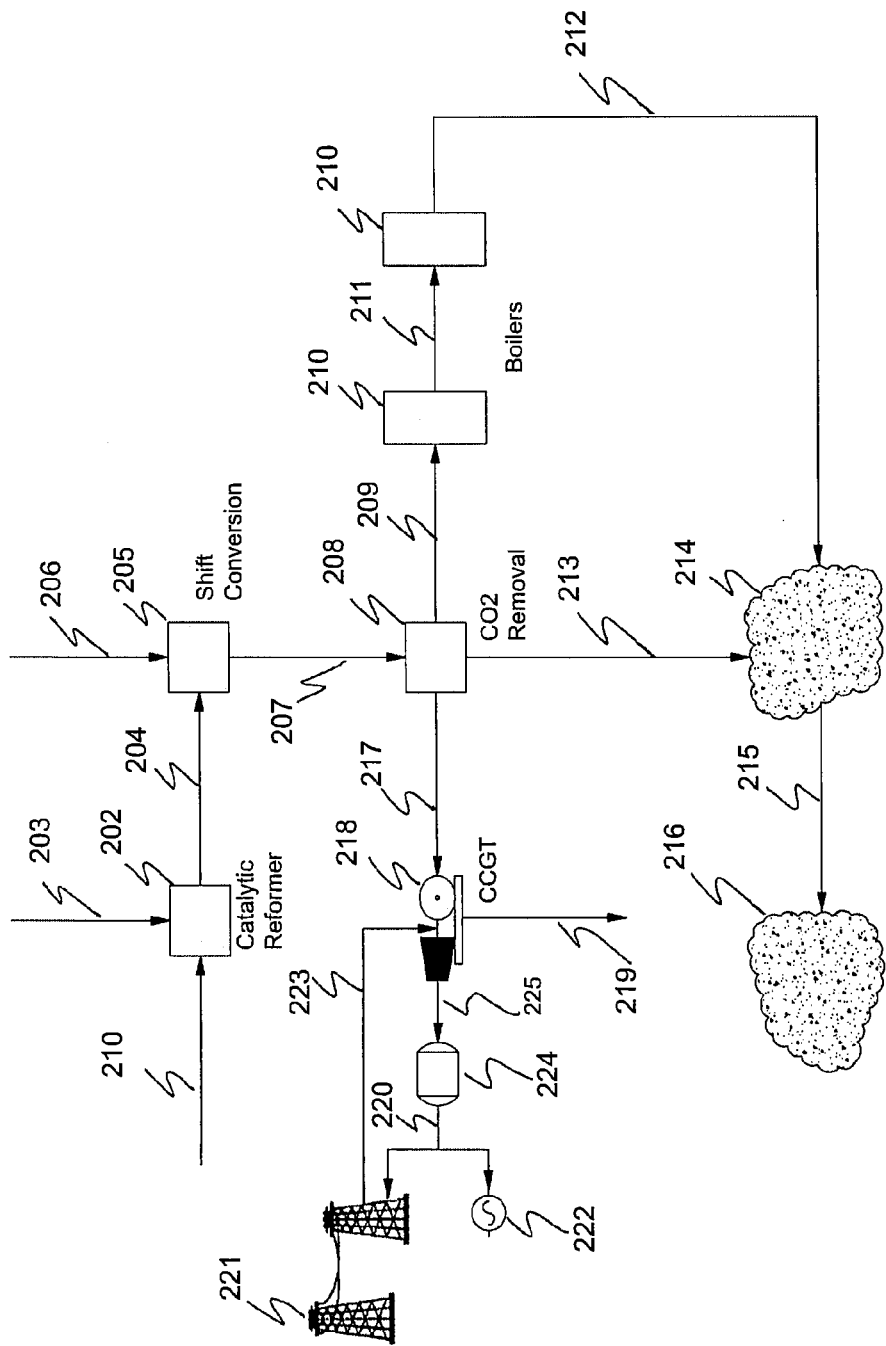
FIG. 2 is a schematic of a flow process for using natural gas to generate power for a thermal recovery operation.
Figure 3:
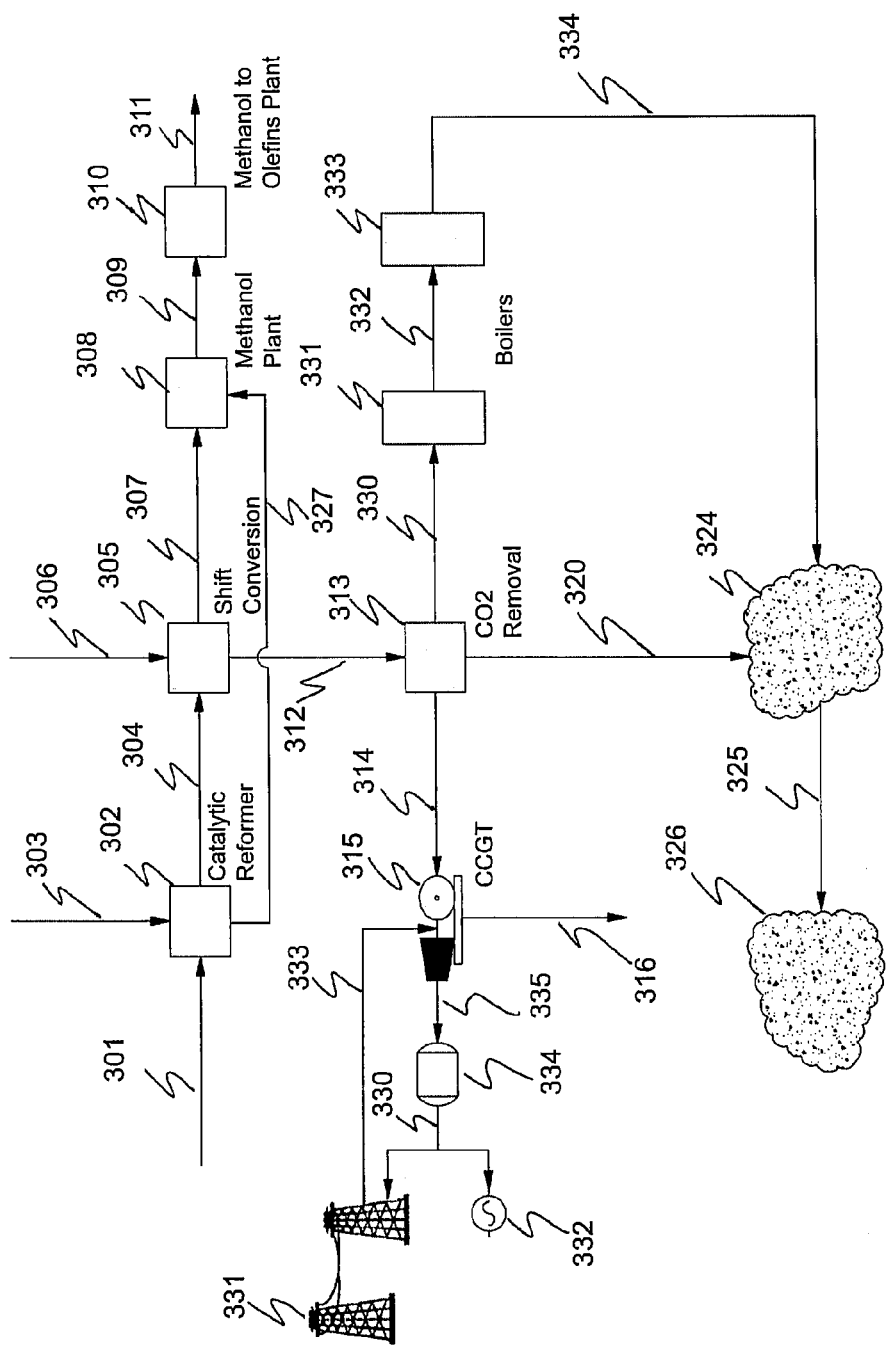
FIG. 3 is a schematic of a flow process for using natural gas to generate power and diluents for a thermal recovery operation.

The high quality methane (about 99% or higher pure methane) in the output gas produced by the carbon dioxide removal and recovery apparatus 145 is then available to be sold or transported to a pipeline 146 or used as a primary fuel for thermal recovery operations such as the process described, for example, in FIGS. 2 and 3.

Natural Gas to Make Molecular Hydrogen

FIG. 2 shows a schematic flow process for using natural gas to generate hydrogen fuel, or a mixture of natural gas and hydrogen, which, in turn, is used to generate electrical power and steam for a thermally assisted recovery operation. In one configuration, the process uses catalytic reformer technology and gasification to generate hydrogen fuel and capture carbon dioxide. This process preferably sequesters at least most, and more preferably almost all, of the carbon dioxide emissions from the various combustion sub-processes. This process can allow heavy oil or bitumen to be recovered by any thermal recovery method while not adding to the fossil carbon dioxide emissions. In other words, it can allow refined oil to be produced from unconventional oil sources, such as bitumen from oil sands, without an extra carbon dioxide emissions burden.

A feed gas 210, which is preferably natural gas comprised primarily of methane ($CH_4$), is supplied as the primary fuel for the process shown in FIG. 2. The feed gas 210 may be supplied by a natural gas pipeline or it may be obtained by another process such as for example that described in FIG. 1. In one configuration, the feed gas 210 is the synthesized gas 116, filtered syngas 121, or treated syngas 123 of FIG. 1. The process of the present invention preferably inputs natural gas in the range of about 10 million to about 200 million standard cubic feet per day (~10 million to ~200 million scfd). This capacity is normally sufficient for a SAGD or HAGD operation outputting approximately 10,000 to 200,000 barrels per day of heavy oil or bitumen.

The feed gas 210 is processed by a catalytic reformer apparatus 202, which requires a supply of steam and air 203. The catalytic reformer apparatus 202 uses well-known reforming technology for manufacturing syngas from methane ($CH_4$). As will be appreciated, the methane can be converted into molecular hydrogen and carbon oxides using other techniques. The output of the catalytic reformer 202 is an output stream 204, comprising from about 30 to about 80 mole percent molecular hydrogen ($H_2$) and from about 20 to about 70 mole percent carbon monoxide (CO).

The output stream 204, in turn, is delivered to a shift conversion apparatus 205 which requires a supply of steam and water 206. The shift conversion apparatus 205 uses well-known shift reaction technology to generate $H_2$ and $CO_2$. As will be appreciated, the methane can be converted into molecular hydrogen and carbon oxides using other techniques.

The output gas 207 of the shift conversion apparatus 205 is a gas stream primarily containing hydrogen and carbon dioxide ($CO_2$). The gas 207, in turn, is delivered to a carbon dioxide capture apparatus 208. The carbon dioxide capture apparatus 208 uses well-known Amine/Rectisol/Selexsol capture technology or other known techniques to capture and remove at least most of the $CO_2$ in the output gas 207 in a waste gas 213 and form a treated gas stream 209 containing at least most of the methane and other hydrocarbons in the output gas 207.

Once the $CO_2$ is captured, it is sent via a first pipeline 213 to an underground reservoir 214 for sequestration. The underground reservoir 214 may be a producing reservoir, an overlying gas cap, a geologic formation not connected with the producing reservoir, or the like. Once sequestered, the $CO_2$ may be delivered by a second pipeline 215 and used for enhanced oil recovery ("EOR") operations 216. As can be appreciated, the $CO_2$ can be delivered directly to an EOR operation from the carbon dioxide capture apparatus 208. The technology for $CO_2$ injection and EOR are proven processes.

A portion 217 of the treated gas stream 209 from the shift conversion apparatus 205 is transferred by path or a third pipeline 217 to a combined cycle gas turbine ("CCGT") 218. As can be appreciated, the manufactured hydrogen can be mixed with the methane to augment its energy content. The hydrogen-fired combined cycle gas turbine is proven technology that can be provided by vendors such as General Electric. The CCGT 218 provides power to an electrical generator 224 which generates electrical power which is delivered via path 220 to electrical transmission lines 221 where it may be sold to the grid. A portion of the electrical energy may be returned via path 223 to provide power for the CCGT 218. The electrical energy produced by generator 224 may be used to power other thermal recovery facilities via path 222 such as, for example, Heat Assisted Gravity Drain ("HAGD") heaters.

The remaining treated gas stream 209 is sent via path or other pipelines 209 and 211 to one or more steam generating boilers 210. The steam generated by boilers 210 may be piped underground to reservoir 214 via path 212 and used for Steam Assisted Gravity Drain ("SAGD") recovery operations. Waste heat from the catalytic reformer, shift reactor and heat recovery steam generators on the gas turbines can be used for SAGD/HAGD steam and energy augmentation.

The process described in FIG. 2 illustrates a method of using natural gas to operate a SAGD or HAGD or combined SAGD/HAGD thermal recovery operation without releasing significant amounts of carbon dioxide into the atmosphere. The process includes sequestering the carbon dioxide underground and, optionally, using a portion or all of the carbon dioxide for EOR purposes.

While the process of FIG. 1 may be used to convert fossil fuels such as coal, bitumen, pet coke, peat, and the like to methane is a stand alone process, it is clear that the methane can then be used in a process such as that of FIG. 2 to generate steam for a thermal process to recover heavy oil or bitumen. Since most, if not all, of the carbon dioxide from both the process of FIG. 1 and the process of FIG. 2 is sequestered, no significant amounts of carbon dioxide are commonly released to the atmosphere.

Either the process of FIG. 2 or the combination of the processes of FIG. 1 and FIG. 2 thus can solve a major problem confronting the production of refined oil from the vast sources of unconventional oil such as heavy oil or bitumen. That problem is the generation of substantial amounts of carbon dioxide released to the atmosphere from the recovery operations alone. For example, the energy equivalent of ¼ to up to ½ a barrel of oil is required to recover a barrel of oil from these unconventional sources by thermal means. When that energy required for recovery produces carbon dioxide, a barrel of refined oil from these sources can be seen to release up to 50% more carbon dioxide to the atmosphere. However, if the processes described herein are used, then this additional release of carbon dioxide is avoided.

Either or both of the processes described herein allow the use of alternate hydrocarbon fuels for in-situ recovery of heavy oil and bitumen without adding additional carbon dioxide emissions to the atmosphere.

Natural Gas to Make Ammonia and/or Methanol

FIG. 3 shows a schematic flow process for using natural gas to generate ammonia fuel, which, in turn, is used to generate electrical power and steam for a thermal recovery operations using catalytic reformer technology and gasification to generate ammonia fuel and capture carbon dioxide. The flow process of FIG. 3 also can include producing methanol which, in turn, is used to produce olefins such as ethylene, propylene and butylene. These processes can be designed to sequester almost all of the carbon dioxide emissions from the various combustion sub-processes. This process can allow heavy oil or bitumen to be recovered by any thermal recovery method while not adding to the fossil carbon dioxide emissions as it can allow refined oil to be produced from unconventional oil sources such as bitumen from oil sands without an extra carbon dioxide emissions burden.

A feed gas 301, such as natural gas comprised primarily of methane ($CH_4$), is supplied as the primary fuel for the process shown in FIG. 3. The feed gas 301 may be natural gas supplied by a natural gas pipeline or it may be obtained by another process such as for example that described in FIG. 1. In one configuration, the feed gas 301 is the treated syngas 123 from the process of FIG. 1. The process of the present invention is typically designed for an input of natural gas in the range of about 10 million to about 200 million standard cubic feet per day (~10 million to ~200 million scfd). This capacity is normally sufficient for a SAGD or HAGD operation outputting approximately 10,000 to 200,000 barrels per day of heavy oil or bitumen. As is well known, other feedstocks may be used as the primary fuel, including LNGs such as propane and butane.

As a common first step to producing ammonia and methanol, any sulfur compounds from the feedstock are removed, such as by sulfur removal apparatus 122, since sulfur deactivates the catalysts used in subsequent steps. Catalytic hydrogenation, for example, converts organo-sulfur compounds into gaseous hydrogen sulfide. The hydrogen sulfide is then removed, for example, by passing the gas through beds of zinc oxide where it is absorbed and converted to solid zinc sulfide.

The feed gas 301 is processed by a catalytic reformer apparatus 302, which requires a supply of steam and air 303. The catalytic reformer apparatus 302 uses well-known reforming technology for manufacturing syngas from methane ($CH_4$). The output of the catalytic reformer 302 is an output stream 304 comprising typically from about 30 to about 80 mole percent hydrogen ($H_2$) and from about 60 to about 70 mole percent carbon oxides (CO and $CO_2$). This stream 304, in turn, is delivered to a shift conversion apparatus 305, which requires a supply of steam and water 306. The output of the catalytic reformer 302 may also be delivered directly to a methanol plant 308 via path 327, where it can be used to produce methanol as described below.

Methanol

The hydrogen and carbon monoxide in the output stream 304 can be transferred directly to a methanol plant 308. The methanol plant 308 uses well-known technology to produce methanol. There are two common processes for producing methanol from hydrogen and carbon monoxide when hydrogen and carbon monoxide are transferred directly from the catalytic reformer 302 to the methanol plant 308. At moderate pressures of 1 to 2 MPa and high temperatures (around 850°

C.), methane reacts with steam on a nickel catalyst to produce syngas. This process is called steam-methane reforming and is endothermic (recovery of a portion of the exothermic heat can be used to assist in generating steam for SAGD for example). Methane can also undergo partial oxidation with molecular oxygen to produce syngas in a reaction that is exothermic. The heat given off can be used in-situ to drive the steam-methane reforming reaction. Carbon monoxide and hydrogen may then react on a second catalyst to produce methanol. The most widely used catalyst is a mixture of copper, zinc oxide, and alumina. At 5 to 10 MPa and 250° C., it can catalyze the production of methanol from carbon monoxide and hydrogen with high selectivity.

The hydrogen and carbon monoxide from the catalytic reformer 302 may also be transferred to a shift conversion apparatus 305 uses well-known shift reaction technology to generate $H_2$ and $CO_2$. The output of the shift conversion apparatus 305 is an output stream 307 of hydrogen ($H_2$) and carbon dioxide ($CO_2$). Some of this output may be delivered via path 307 to a methanol plant 308, where it undergoes autothermal reforming. The ratio of CO and H2 can be adjusted by using the water-gas shift reaction to provide the appropriate stoichiometry for methanol synthesis.

The methanol-containing product 309 produced in methanol plant 308 is then transferred via path 309 to a methanol-to-olefins plant 310 where olefins, such as ethylene $C_2H_4$, propylene $C_3H_6$, butylene $C_4H_8$ and pentylene $C_5H_{10}$ are produced. The olefins may be used as diluents in bitumen recovery utilizing the VAPEX process; used in preparing recovered bitumen for pipeline transport; and/or may be sold as a product.

Ammonia

Optionally, the remainder 312 of the hydrogen and carbon dioxide output from shift conversion apparatus 305 is delivered via path 312 to an ammonia plant 313 where it is converted into an ammonia fuel. The carbon dioxide is then removed, for example, either by absorption in aqueous ethanolamine solutions or by adsorption in pressure swing adsorbers (PSA) using proprietary solid adsorption media. Other techniques may also be employed. A final step in processing the input hydrogen is to use catalytic methanation to remove any small residual amounts of carbon monoxide or carbon dioxide from the hydrogen.

To produce the desired end-product ammonia, at least most of the molecular hydrogen in the remainder 312 is then catalytically reacted with nitrogen (derived from process air) to form anhydrous liquid ammonia. This step is known as the ammonia synthesis loop and may also be referred to as the Haber-Bosch process.

The steam reforming, shift conversion, carbon dioxide removal and methanation steps each operate at absolute pressures of about 25 to 35 bar, and the ammonia synthesis loop operates at absolute pressures ranging from 60 to 180 bar, depending upon which proprietary design is used.

A portion of the ammonia-containing product produced in ammonia plant 313 is sent via path or pipeline 330 and 332 to one or more steam generating boilers 331 and 333. The steam generated by boilers 331 and 333 may be piped underground via path 334 and used for Steam Assisted Gravity Drain ("SAGD") recovery operations.

A second portion of the ammonia-containing product produced in ammonia plant 313 is sent by path or pipeline 314 to a combined cycle gas turbine ("CCGT") 315. The ammonia-fired combined cycle gas turbine is proven technology that can be provided by vendors such as General Electric. The CCGT 315 provides power to an electrical generator 334 which generates electrical power which is delivered via path 330 to electrical transmission lines 331 where it may be sold to the grid. A portion of the electrical energy may be returned via path 333 to provide power for the CCGT 318. The electrical energy produced by generator 334 may be used to power other thermal recovery facilities via path 332 such as, for example, Heat Assisted Gravity Drain ("HAGD") heaters.

A portion of the ammonia may also be sold as fertilizer to obtain carbon dioxide offsets through accelerated growth of the fertilized crops.

The $CO_2$ captured in the ammonia plant 313 as a waste gas, separate from the ammonia-containing product, is sent via path 320 to an underground reservoir 324 for sequestration. The underground reservoir may be a producing reservoir, an overlying gas cap, a geologic formation not connected with the producing reservoir, or the like. Once sequestered, the $CO_2$ may be delivered by pipeline 325 and used for enhanced oil recovery ("EOR") operations. As can be appreciated, the $CO_2$ can be delivered directly to an EOR operation from the carbon dioxide capture apparatus. The technology for $CO_2$ injection and EOR are proven processes.

The process described in FIG. 3 illustrates a method of using natural gas to operate a SAGD or HAGD or combined SAGD/HAGD thermal recovery operation without releasing significant amounts of carbon dioxide into the atmosphere. The process includes sequestering the carbon dioxide underground and, optionally, using a portion or all of the carbon dioxide for EOR purposes.

While the process of FIG. 1 may be used to convert fossil fuels such as coal, bitumen, pet coke, peat, and the like to methane is a stand alone process, it is clear that the methane can then be used in a process such as that of FIG. 3 to generate steam for a thermal process to recover heavy oil or bitumen. Since the carbon dioxide from both the process of FIG. 3 and the process of FIG. 1 is sequestered, no significant amounts of carbon dioxide are released to the atmosphere.

Either the process of FIG. 3 or the combination of the processes of FIG. 3 and FIG. 1 thus can solve a major problem confronting the production of refined oil from the vast sources of unconventional oil such as heavy oil or bitumen. That problem is the generation of substantial amounts of carbon dioxide released to the atmosphere from the recovery operations alone. For example, the energy equivalent of ¼ to up to ½ a barrel of oil is required to recover a barrel of oil from these unconventional sources by thermal means. If that energy required for recovery produces carbon dioxide then a barrel of refined oil from these sources can be seen to release up to 50% more carbon dioxide to the atmosphere. However, if the processes described herein are used, then this additional release of carbon dioxide is avoided.

Using the above processes, most of the carbon dioxide produced during extraction of hydrocarbons by thermal techniques, such as SAGD or HAGD, from subsurface deposits and formations can be captured and sequestered in a selected location, such as an underground formation. In a typical application, at least most, more typically at least about 75%, and even more typically at least about 90% of the carbon dioxide produced during extraction of hydrocarbons is captured and sequestered.

A number of variations and modifications of the invention can be used. As will be appreciated, it would be possible to provide for some features of the invention without providing others.

The present invention, in various embodiments, includes components, methods, processes, systems and/or apparatus substantially as depicted and described herein, including various embodiments, sub-combinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, for example for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method, comprising:
    (a) converting a hydrocarbon fuel into a synthesized gas comprising methane and other hydrocarbons, molecular hydrogen, sulfur compounds, and carbon oxides;
    (b) removing sulfur compounds from the synthesized gas to form a treated synthesized gas comprising at least most of the hydrocarbons, molecular hydrogen, and carbon oxides in the synthesized gas and a waste gas comprising at least most of the sulfur compounds in the synthesized gas;
    (c) converting molecular hydrogen and carbon oxides in the treated synthesized gas into methane to form a product gas, the product gas comprising carbon oxides and methane;
    (d) removing at least most of the carbon oxides from the product gas to form an output gas comprising at least most of the methane in the product gas and a second waste gas comprising at least most of the carbon oxides in the product gas; and
    (e) combusting at least a portion of the output gas and/or a fuel derived therefrom to provide energy for in-situ recovery of a fossil fuel source from a subsurface formation.

2. The method of claim 1, wherein steps (a)-(e) are performed on a site positioned above the subsurface formation and wherein at least most of the carbon oxides are sequestered in a selected subsurface formation.

3. The method of claim 1, wherein the synthesized gas, after step (a) and before step (b), is contacted in a heat exchanger with water to reduce a temperature of the synthesized gas and convert the water into steam, at least a portion of the steam being provided to a steam turbine to provide energy for use in in-situ recovery of the fossil fuel source.

4. The method of claim 3, wherein, after being outputted by the heat exchanger, at least most of the particulates in the synthesized gas are removed to form a filtered synthesized gas.

5. The method of claim 3, wherein step (c) is performed by methanation and wherein, prior to step (c), the treated synthesized gas is contacted with a portion of the steam from the heat exchanger and wherein a portion of the steam is used in step (c) to convert molecular hydrogen and carbon oxides into methane.

6. The method of claim 1, wherein the fossil fuel source is at least one of bitumen, kerogen, and heavy crude oil and wherein the hydrocarbon fuel is at least one of coal, peat, bitumen, and petroleum coke.

7. A method, comprising:
    (a) converting a hydrocarbon fuel into a synthesized gas comprising methane and other hydrocarbons, molecular hydrogen, sulfur compounds, and carbon oxides;
    (b) removing sulfur compounds from the synthesized gas to form a treated synthesized gas comprising at least most of the hydrocarbons, molecular hydrogen, and carbon oxides in the synthesized gas and a waste gas comprising at least most of the sulfur compounds in the synthesized gas;
    (c) converting methane in the treated synthesized gas into molecular hydrogen and carbon oxides to form a product gas, the product gas comprising carbon oxides and molecular hydrogen;
    (d) removing at least most of the carbon oxides from the product gas to form an output gas comprising at least most of the molecular hydrogen in the product gas and a second waste gas comprising at least most of the carbon oxides in the product gas; and
    (e) combusting at least a portion of the output gas and/or a fuel derived therefrom to provide energy for in-situ recovery of a fossil fuel source from a subsurface formation.

8. The method of claim 7, wherein steps (a)-(e) are performed on a site positioned above the subsurface formation and wherein at least most of the carbon oxides are sequestered in a selected subsurface formation.

9. The method of claim 7, wherein step (c) comprises the sub-steps:
    (C1) converting, by a catalytic reformer unit, a first portion of the methane into molecular hydrogen and carbon oxides in an intermediate product gas; and
    (C2) converting, by a shift conversion unit, a second portion of the methane into molecular hydrogen and carbon oxides in the product gas.

10. The method of claim 7, wherein the hydrocarbon fossil fuel source is at least one of bitumen, kerogen, coal and heavy crude oil and wherein the hydrocarbon fuel is at least one of peat, bitumen, asphaltene and petroleum coke.

11. A method, comprising:
    (a) converting a hydrocarbon fuel into a synthesized gas comprising methane and other hydrocarbons, molecular hydrogen, sulfur compounds, and carbon oxides;
    (b) removing sulfur compounds from the synthesized gas to form a treated synthesized gas comprising at least most of the hydrocarbons, molecular hydrogen, and carbon oxides in the synthesized gas and a first waste gas comprising at least most of the sulfur compounds in the synthesized gas;

(c) converting methane in the treated synthesized gas into molecular hydrogen and carbon oxides to form a product gas, the product gas comprising carbon oxides and molecular hydrogen;

(d) converting a portion of the molecular hydrogen into an output gas comprising predominantly ammonia;

(e) removing at least most of the carbon oxides from the product gas to form a second waste gas comprising at least most of the carbon oxides in the product gas; and (f) combusting at least a portion of the output gas and/or a fuel derived therefrom to provide energy for in-situ recovery of a fossil fuel source from a subsurface formation.

12. The method of claim 11, wherein steps (a)-(f) are performed on a site positioned above the subsurface formation and wherein at least most of the carbon oxides are sequestered in a selected subsurface formation.

13. The method of claim 11, wherein step (c) comprises the sub-steps:
(C1) converting, by a catalytic reformer unit, a first portion of the methane into molecular hydrogen and carbon oxides in an intermediate product gas; and
(C2) converting, by a shift conversion unit, a second portion of the methane into molecular hydrogen and carbon oxides in the product gas.

14. The method of claim 11, wherein the fossil fuel source is at least one of bitumen, kerogen, coal and heavy crude oil and wherein the hydrocarbon fuel is at least one of peat, bitumen, asphaltene and petroleum coke.

15. The method of claim 11, wherein the fossil fuel source is bitumen or heavy oil and further comprising:
(g) converting at least a portion of the molecular hydrogen in the product gas into methanol; and
(h) converting at least most of the methanol into olefins, wherein the olefins are used as diluents in bitumen recovery;
(i) utilizing a portion of the carbon dioxide and converting at least most of the methanol into olefins, wherein the olefins and carbon dioxide are used as diluents in heavy oil recovery.

16. A method, comprising:
(a) converting a hydrocarbon fuel into a synthesized gas comprising methane and other hydrocarbons, molecular hydrogen, sulfur compounds, and carbon oxides;
(b) removing sulfur compounds from the synthesized gas to form a treated synthesized gas comprising at least most of the hydrocarbons, molecular hydrogen, and carbon oxides in the synthesized gas and a first waste gas comprising at least most of the sulfur compounds in the synthesized gas;
(c) converting methane in the treated synthesized gas into molecular hydrogen and carbon oxides to form a product gas, the product gas comprising carbon oxides and molecular hydrogen;
(d) converting at least a portion of the molecular hydrogen in the product gas into methanol; and
(e) converting at least most of the methanol into olefins, wherein the olefins are used as diluents in bitumen recovery.

17. The method of claim 16, further comprising:
(f) converting a portion of the molecular hydrogen into an output gas comprising predominantly ammonia;
(g) removing at least most of the carbon oxides from the product gas to form a second waste gas comprising at least most of the carbon oxides in the product gas; and
(h) combusting at least a portion of the output gas and/or a fuel derived therefrom to provide energy for thermally assisted recovery of a fossil fuel source from a subsurface formation.

18. The method of claim 17, wherein steps (a)-(h) are performed on a site positioned above the subsurface formation and wherein at least most of the carbon oxides are sequestered in a selected subsurface formation.

19. The method of claim 16, wherein step (c) comprises the sub-steps:
(C1) converting, by a catalytic reformer unit, a first portion of the methane into molecular hydrogen and carbon oxides in an intermediate product gas; and
(C2) converting, by a shift conversion unit, a second portion of the methane into molecular hydrogen and carbon oxides in the product gas.

20. The method of claim 16, wherein the fossil fuel source is at least one of bitumen, kerogen, coal and heavy crude oil and wherein the hydrocarbon fuel is at least one of peat, bitumen, asphaltene and petroleum coke.

21. A method, comprising:
(a) converting bitumen or heavy oil into a synthesized gas comprising methane and other hydrocarbons, molecular hydrogen, sulfur compounds, and carbon oxides;
(b) removing sulfur compounds from the synthesized gas to form a treated synthesized gas comprising at least most of the hydrocarbons, molecular hydrogen, and carbon oxides in the synthesized gas and a first waste gas comprising at least most of the sulfur compounds in the synthesized gas;
(c) converting a portion of the methane in the treated synthesized gas into molecular hydrogen and carbon oxides to form product gases, the product gases comprising methane, molecular hydrogen and carbon oxides;
(d) converting at least a portion of the molecular hydrogen in the product gas into methanol;
(e) converting at least most of the methanol into olefins, wherein the olefins are in the form of diluents;
(f) combusting a portion of at least one of methane and molecular hydrogen to generate electrical power;
(g) converting carbon oxides to form a second waste gas, the second waste gas comprising carbon oxides and wherein at least most of the carbon oxides are sequestered in a selected subsurface formation; and
(h) selling the electrical power, diluents and methane as products wherein most of the carbon from producing these products has been removed.

* * * * *